United States Patent [19]

Olsen

[11] Patent Number: 4,837,015
[45] Date of Patent: Jun. 6, 1989

[54] ALKALI METAL ION-CHARGED, CATION EXCHANGER AND USE THEREOF TO ADJUST SODIUM, POTASSIUM AND CALCIUM BODY FLUID LEVELS

[75] Inventor: James L. Olsen, Chapel Hill, N.C.

[73] Assignee: Carolina Medical Products Company, Inc., Chapel Hill, N.C.

[21] Appl. No.: 22,021

[22] Filed: Mar. 5, 1987

[51] Int. Cl.$^4$ .................................. A61K 31/74
[52] U.S. Cl. ........................................... 424/79
[58] Field of Search .......................... 424/81, 79

[56] References Cited

U.S. PATENT DOCUMENTS 4,623,539  11/1986  Tunc .................................. 424/79

Primary Examiner—Joseph L. Slchofer
Assistant Examiner—Peter F. Kulkosky
Attorney, Agent, or Firm—Timothy R. Kroboth

[57] ABSTRACT

A novel alkali metal cation-charged, cation exchange resin is provided. The resin includes about 15–50 mEq % of calcium ion, and about 5–13 mEq % of magnesium ion. The calcium ion and magnesium ion loading prevent serious depletion of alkaline earth metal values from body fluids. Also provided is a method of treating a host having hypernatremia or hyperkalemia, using the resin. In one embodiment, the resin includes a supplementary amount of bioavailable calcium ion.

20 Claims, No Drawings

ALKALI METAL ION-CHARGED, CATION EXCHANGER AND USE THEREOF TO ADJUST SODIUM, POTASSIUM AND CALCIUM BODY FLUID LEVELS

TECHNICAL FIELD

The present invention relates to a pharmaceutical composition for adjusting cation levels in body fluids. In one embodiment, the composition includes a supplementary amount of bioavailable calcium ion.

BACKGROUND ART

A high sodium ion level in plasma and other extracellular body fluids, is a problem frequently found in patients undergoing treatment with diuretics for elevated blood pressure. Patients with high sodium ion levels, typically also have low potassium ion levels. Accordingly, a pharmaceutical composition that provides for the exchange of potassium ion for sodium ion, advantageously treats both abnormalities. Unlike conventional potassium supplements such as a potassium chloride elixir, this type of pharmaceutical composition has the further advantage of not increasing the total ionic load of sodium and potassium.

In other patients, a high potassium ion level in the body fluids, is a problem. Sodium polystyrene sulfonate ion exchange resin is often administered to reduce potassium ion levels in these hyperkalemic patients. The resin is not bioabsorbable. Typically, the resin is given orally, but may be administered rectally.

Four years ago, sales of calcium supplements totaled $47 million. Now, the figure is closer to $200 million a year, as the public has responded to the 1984 NIH recommendation of 1000 mg a day to prevent osteoporosis. Postmenopausal women, particularly thin, white women, are most at risk. A drawback of certain calcium supplements is a lack of bioavailability of the calcium.

As illustrated by U.S. Pat. No. 4,395,392 to Wolgemuth, oral administration of a certain water-soluble vinylbenzenesulfonic acid polymer, decreases urinary calcium content.

As exemplified by U.S. Pat. No. 4,542,015 to Smakman et al, the phosphate level in the blood of a patient requiring dialysis, may be reduced by using in the clearance department of a dialysis apparatus, a cation exchanger charged with ferric ions and alkali metal ions. In place of ferric ions, ions of thorium, tin, lanthanum, aluminum or zirconium metal may be used. In a preferred embodiment, the cation exchanger is also charged with alkaline earth metals. In one embodiment, the charged cation exchanger may be orally administered in capsule form.

As described by U.S. Pat. No. 2,611,730 to Heming, a high sodium ion level in body fluids may be reduced by the oral administration of a cation exchange resin, and it has been observed that the use of resins has resulted in depleted blood levels of calcium and potassium. Heming's detailed description shows cation exchangers having a loading of calcium within the normal electrolyte range. Furthermore, Heming's exemplary resins are charged with a physiologically insignificant cation or with an amino acid, said to be physiologically insignificant.

I have surprisingly discovered that an alkali metal cation-charged, cation exchange resin having a loading of an alkaline earth metal within the normal electrolyte range, will seriously deplete alkaline earth metal cations from body fluids. Therefore, there is a need for an alkali metal cation-charged, cation exchange resin that prevents serious depletion of calcium and magnesium cations from body fluids. There is an even greater need for a resin of this type that maintains the calcium and magnesium values within the normal electrolyte ranges.

If charged with potassium, such a cation exchanger would exchange potassium for sodium, and therefore be useful for reducing the body level of sodium and increasing the potassium level. If charged with sodium, such a cation exchange resin would exchange sodium for potassium, and accordingly be useful for reducing the body level of potassium. Thus, the discovery of such an alkali metal cation-charged, cation exchanger would constitute a significant contribution to the medical art. Such a cation exchanger would contribute even further to the medical art if it also had utility in treating hypocalcemic patients.

DISCLOSURE OF THE INVENTION

It is accordingly an object of the present invention to provide a novel alkali metal cation-charged, cation exchange resin that prevents serious depletion of calcium and magnesium cations from body fluids.

It is a further object of the present invention to provide a cation exchanger of this type that is charged with potassium ion and thus useful for treating hypernatremia and hypokalemia.

It is an even further object to provide a cation exchange resin of this type that is charged with sodium ion and therefore has utility in the treatment of the hyperkalemic patient.

It is a still further object to provide an improved alkali metal cation-charged, cation exchanger that provides a supplement of bioavailable calcium ion.

Additional objects, advantages and novel features of the present invention are set forth in the description that follows, and in part will become apparent to those skilled in the art upon examination of the following description or may be learned by practice of the invention.

To achieve the foregoing objects and in accordance with the purpose of the present invention, as embodied and broadly described herein, there is provided a pharmaceutical composition that may be broadly described as including a cation exchange resin and a pharmaceutically acceptable carrier. The resin, which is not bioabsorbable, is charged with about 80-40 mEq % of an alkali metal ion, about 15-50 mEq % of calcium ion, and about 5-13 mEq % of magnesium ion. The alkali metal is sodium or potassium. The resin is useful for treating hypernatremic or hyperkalemic patients.

In an embodiment useful for treating patients also having low calcium blood levels, the resin is charged with about 35-50 mEq % of calcium ion.

Also provided by the present invention is a method for decreasing sodium body fluid levels and increasing potassium body fluid levels. The treatment includes administering to a patient in need of such treatment, a therapeutically effective amount of the pharmaceutical composition, in which the alkali metal cation is potassium.

The invention additionally provides a method for decreasing sodium body fluid levels, increasing potassium body fluid levels, and increasing calcium body fluid levels. In the treatment, a therapeutically effective amount of the pharmaceutical composition, in which the alkali metal cation is potassium and the resin is charged with about 35–50 mEq % of calcium ion, is administered to a patient in need of such treatment.

In addition, there is provided a method for decreasing potassium body fluid levels. This method includes administering to a patient in need of such treatment, a therapeutically effective amount of the pharmaceutical composition, in which the alkali metal cation is sodium.

Also, there is provided a method for decreasing potassium body fluid levels and increasing calcium body fluid levels. In this method, a therapeutically effective amount of the pharmaceutical composition, in which the alkali metal cation is sodium and the resin is charged with about 35–50 mEq % of calcium ion, is administered to a patient in need of such treatment.

BEST MODE FOR CARRYING OUT THE INVENTION

As explained earlier, the present invention is directed to a novel alkali metal cation-charged, cation exchange resin that prevents serious depletion of calcium and magnesium cations from body fluids. When charged with potassium, this unique cation exchanger exchanges potassium for sodium, and is therefore highly useful for treating a patient having high sodium and low potassium values in the body fluids. When charged with sodium, the resin exchanges sodium for potassium, and is accordingly useful for reducing the potassium level in body fluids. Normal electrolyte ranges are 135–148 mEq/L for sodium ion, and 3.5–5.5 mEq/L for potassium ion. Advantageously, a resin in accordance with my invention, does not increase the total ionic load of potassium and sodium.

Preferably, the cation exchanger maintains calcium and magnesium cations within normal electrolyte ranges. Normal electrolyte ranges are 4.2–5.3 mEq/L for calcium ion, and 1.5–2.0 mEq/L for magnesium ion. Hence, it is preferred that the cation exchanger is loaded with sufficient calcium and magnesium to maintain these normal electrolyte ranges.

Cation exchange resins useful in my invention are conventional in the medical art, and have a pharmaceutical grade of purity. These resins are characterized by not being bioabsorbable, and may be water insoluble. Accordingly, resins suitable for use in my invention, pass through the gastrointestinal tract unaffected by digestion, and without exerting any physiological impact other than the exchange of cations.

Strongly acidic cation exchangers are especially suitable, with sulfonic resins being illustrative. A preferred sulfonic resin is made by polymerization of styrene with divinylbenzene, a cross-linking agent.

An exemplary sodium salt of a styrene/divinylbenzene sulfonic acid resin containing 8% divinylbenzene (commonly known as sodium polystyrene sulfonate) is available in the form of beads under the name Ionac C-269, from Sybron Chemicals Inc. Alternatively, the powder form of sodium polystyrene sulfonate could be used, and may be obtained under the name Amberlite IRP-69 from Rohm and Haas Co. Suitably, the powder may have a particle size of about 100–500 mesh.

As explained earlier, a cation exchanger useful in my invention is charged with either potassium or sodium ions, and with calcium and magnesium ions. Useful sources of these cations are KCl for potassium, NaCl for sodium, $CaCl_2.2H_2O$ for calcium, and $MgCl_2.6H_2O$ for magnesium.

The cation exchange resin is loaded with the desired cations in any suitable manner. To this end, the cation exchanger starting material may be in a suitable form such as the acid form or entirely or partly in a salt form, for instance the sodium salt form. Charging is effected in a known manner, for instance by means of an aqueous solution of a salt of the cations to be loaded onto the resin. The charging time is suitably about 30 minutes.

For purposes of illustration, to prepare a resin charged with 60 mEq % K ion, 30 mEq % Ca ion and 10 mEq % Mg ion, the sodium form of the resin is equilibrated with an aqueous solution containing the three desired cations in the foregoing proportions (17.9 g/L KCl, 8.8 g/L $CaCl_2.2H_2O$, and 4.1 g/L $MgCl_2.6H_2O$). Typically, the resin is equilibrated with several portions of the aqueous treatment solution, and after equilibration with the last portion of treatment solution, rinsed with distilled water.

Unlike Heming's medical preparation, I prefer to load the cation exchanger substantially full of physiologically active cations, in order to provide the charged resin with as high a loading of these cations per gram of resin, as possible. Thus, I charge the resin with about 80–40 mEq %, preferably about 75–50 mEq %, of sodium or potassium, and would not charge the resin with a physiologically insignificant species such as ammonium cation. Therefore, my preferred cation-charged resin is substantially free of physiologically insignificant species. My use of the term "physiologically insignificant" is intended to convey the same meaning as intended by Heming. By the term "substantially full" I mean that the preferred cation-charged resin is at least about 98% loaded, and by the term "substantially free" I mean that the preferred cation-charged resin includes about 2 mEq % or less of physiologically insignificant species.

A critical feature of my invention is that the resin is charged with about 15–50 mEq % of calcium ion, and about 5–13 mEq % of magnesium ion. I have discovered that to prevent serious depletion of calcium and magnesium cations, a loading of calcium and magnesium within these ranges is necessary. Thus, the charge of the alkali metal cation is limited by the loading of alkaline earth metal cation needed to prevent serious alkaline earth metal depletion.

Except in the case of the hypocalcemic patient, the resin is charged with preferably about 20–38 mEq %, very preferably about 29–33 mEq %, of calcium ion, and with preferably about 7–13 mEq %, very preferably about 9–12 mEq of magnesium ion. For the patient who is also hypocalcemic, it is preferred to administer a resin in accordance with the invention, that is charged with about 37–50 mEq % of calcium ion.

The charged cation exchanger of the present invention can be orally administered as a tablet or in suspension form. The daily dosage will vary over a wide range depending upon, for instance, the severity of the hyperkalemia or hypernatremia, and should be titrated to the individual disease by monitoring blood values and adjusting the dosage as necessary. An advantage of the exchanger is that the amount of alkali metal cation removed by exchange, may be calculated. Alternatively, the exchanger may be administered rectally as an enema, or introduced directly into the stomach through a plastic tube.

If the patient is also hypocalcemic, the cation exchanger of the present invention charged with about 37–50 mEq % of calcium ion, may be advantageously administered. The bioavailability of the calcium ion is an important benefit of this drug.

For a potassium or sodium polystyrene sulfonate resin charged with calcium and magnesium in accordance with the present invention, a 60 ml suspension containing about 15 g of the resin and about 20 ml of sorbitol for preventing constipation, is very useful. Other suspension ingredients typically include, in decreasing amounts as now listed, ethyl alcohol, water, propylene glycol, veegum, sodium saccharin, methylparaben, propylparaben and flavor. A tablet containing about 1 g of the resin and conventional inactive ingredients such as lactose and corn starch, may also be used.

A suitable dosage for adults ranges from about 15 g to 60 g of the resin. Thus, 15 g of resin suspension could be administered one to four times daily.

In the Examples that follow and throughout this description and the claims set forth below, all percentages are by weight/weight, and all procedures are carried out at ambient temperature and pressure, unless otherwise specified.

EXAMPLE 1

20 g of sodium polystyrene sulfonate resin ion exchange beads (made from monomeric styrene crosslinked with 8% divinylbenzene), available from Sybron Chemicals Inc. as Sybron-Ionac C269, is mixed with a 50 ml portion of an aqueous solution containing 80 mEq % K, 15 mEq % Ca, and 5 mEq % Mg, and allowed to equilibrate for 30 minutes. The solution is decanted, and the treatment step is repeated three times using a fresh 50 ml portion each time, to produce a treated resin. The ion loading on the treated resin is 80 mEq % K, 15 mEq % Ca and 5 mEq % Mg.

Normal electrolyte solution containing 138 mEq Na, 4.2 mEq K, 4.9 mEq Ca, and 1.75 mEq Mg per liter, is prepared by dissolving 8.08 g NaCl, 0.31 g KCl, 0.36 g $CaCl_2.2H_2O$, and 0.18 g $MgCl_2.6H_2O$ in 1 liter of water. By the term "normal" is meant with regard to this electrolyte solution, that the cation values are within the normal electrolyte ranges for humans.

The treated resin is placed in a column, washed with distilled water, and eluted with 50 ml portions of the normal electrolyte solution. The ion values of the normal electrolyte solution, as determined by analysis, are contained in Table 1, in which the designation "Normal" is used.

Each 50 ml portion of the normal electrolyte solution is allowed to equilibrate with the resin for 15 minutes, after which the column stopcock is opened to provide a slow drip. Each 50 ml eluant is collected, and selected eluants are analyzed.

The results are expressed in Table 1 as mEq/L of ion, with portion "1" being the first 50 ml portion to pass through the column, portion "4" being the fourth 50 ml portion to pass through the column, and so forth.

COMPARATIVE EXAMPLE 1

The resin starting material of Example 1, is converted to a treated resin with an ion loading of 100 mEq % K. Following the procedure of Example 1, the treated resin is equilibrated with 50 ml portions of the normal electrolyte solution of Example 1, each 50 ml eluant is collected, and selected eluants are analyzed. The ion values of the normal electrolyte solution, as determined by analysis, are set forth in Table 2 (see the designation "Normal").

Table 2 shows the results, which are expressed as mEq/L of ion. Portion "1" is the first 50 ml portion to pass through the column, portion "2" is the second 50 ml portion to pass through the column, and so forth. These results demonstrate that an alkali metal ion-charged, cation exchanger charged with the alkali metal ion only, seriously depletes calcium and magnesium values.

TABLE 1#

| Portion | Na | K | Ca | Mg |
|---|---|---|---|---|
| Normal | 134.0 | 4.3 | 5.0 | 1.6 |
| 1 | 10.0 | 103.0 | 1.7 | 0.5 |
| 4 | 20.0 | 130.0 | 2.3 | 0.7 |
| 8 | 80.0 | 74.0 | 2.0 | 0.7 |

Results expressed as mEq/L of the ion

TABLE 2

| Portion | Na | K | Ca | Mg |
|---|---|---|---|---|
| Normal | 143.0 | 4.4 | 4.8 | 1.6 |
| 1 | 53.0 | 122.0 | 0.05 | <1 |
| 2 | 52.0 | 146.0 | 0.15 | <1 |
| 3 | 51.0 | 154.0 | 0.1 | <0.1 |

TABLE 3

| Portion | Ca | Mg |
|---|---|---|
| Normal | 4.9 | 1.5 |
| 1 | 0.6 | 0.3 |
| 2 | 0.8 | 0.4 |
| 5 | 0.7 | 0.4 |

COMPARATIVE EXAMPLE 2

20 g of the resin starting material of Example 1, is mixed with a 20 ml portion of an aqueous solution containing 95.4 mEq % K (144 mEq K, 18.2 g KCl per 100 ml), 3.3 mEq % Ca (5 mEq Ca, 1.2 g $CaCl_2.2H_2O$ per 100 ml) and 1.3 mEq % Mg (2 mEq Mg, 1.1 g $MgCl_2.6H_2O$ per 100 ml), and allowed to equilibrate for 30 minutes. The solution is decanted, and the treatment step is repeated four times using a fresh 20 ml portion each time, to produce a treated resin. The ion loading on the treated resin is 95.4 mEq % K, 3.3 mEq % Ca and 1.3 mEq % Mg.

Following the procedure of Example 1, the treated resin is equilibrated with 50 ml portions of the normal electrolyte solution of Example 1, each 50 ml eluant is collected, and selected eluants are analyzed. The Ca and Mg ion values of the normal electrolyte solution, as determined by analysis, are set forth in Table 3 (see the designation "Normal").

The results are shown in Table 3 as mEq/L of ion. Portion "1" is the first 50 ml portion to pass through the column, portion "2" is the second 50 ml portion to pass through the column, and so forth. These results surprisingly demonstrate that an alkali metal ion-charged, cation exchanger with a loading of calcium and magnesium within the normal electrolyte ranges, seriously depletes calcium and magnesium values.

EXAMPLE 2

10 g of the resin starting material of Example 1, is converted to a treated resin having the ion loading (mEq %) shown in Table 4. The treatment is effected using 1-40 ml and 3-20 ml portions of an aqueous solution containing appropriate amounts of KCl, $CaCl_2.2H_2O$ and $MgCl_2.6H_2O$.

The treated resin is placed in a column and washed with distilled water. The resin is then eluted with 25 ml portions of the normal electrolyte solution of Example 1. The Ca ion value (mEq/L) of the normal electrolyte solution, as determined by analysis, is found in Table 5, in which the designation "Normal" is used. Each 25 ml portion of the normal electrolyte solution is allowed to equilibrate with the resin for 15 minutes, after which the column stopcock is opened to provide a slow drip. Each 25 ml eluant is collected, and selected eluants are analyzed.

The results are shown in Table 5, as mEq/L of Ca ion. Portion "1" is the first 25 ml portion to pass through the column, portion "2" is the second 25 ml portion to pass through the column, and so forth.

EXAMPLES 3-11

In accordance with the procedure of Example 2, nine samples of the resin starting material of Example 1, each weighing 10 g, are converted to nine treated resins having the ion loading (mEq %) shown in Table 4.

Again following the procedure of Example 2, each treated resin is equilibrated with 25 ml portions of the normal electrolyte solution, each 25 ml eluant is collected, and selected eluants are analyzed for each treated resin. Ca ion values of the normal electrolyte solution, as determined by analysis, are set forth in Table 5 (see the designation "Normal"). The results are shown in Table 5, as mEq/L of Ca ion.

TABLE 4

| | Ion Loading on Resin (mEq %) | | |
|---|---|---|---|
| Example | K | Ca | Mg |
| 2 | 73 | 20 | 7 |
| 3 | 68 | 25 | 7 |
| 4 | 60 | 30 | 10 |
| 5 | 56.8 | 31.6 | 11.6 |
| 6 | 56.8 | 31.6 | 11.6 |
| 7 | 56.8 | 31.6 | 11.6 |
| 8 | 52.5 | 35.5 | 12 |
| 9 | 52 | 36 | 12 |
| 10 | 50 | 37.5 | 12.5 |
| 11 | 47 | 40 | 13 |

TABLE 5*

| | Example | | | | | | | | | |
|---|---|---|---|---|---|---|---|---|---|---|
| Portion | 2 | 3 | 4 | 5 | 6 | 7 | 8 | 9 | 10 | 11 |
| Normal | 4.9 | 5.0 | 4.8 | 5.1 | 5.1 | 5.0 | 5.1 | 5.0 | 5.0 | 5.0 |
| 1 | 1.9 | 8.1 | 6.1 | 5.4 | 3.4 | 6.8 | 5.7 | 8.1 | 10.1 | 11.3 |
| 2 | 2.0 | 3.3 | 5.3 | 5.8 | 3.9 | 5.3 | 5.2 | 6.3 | 8.7 | 8.4 |
| 5 | 1.7 | 3.1 | 4.3 | 4.8 | 3.0 | 4.8 | 4.6 | 5.3 | 6.9 | 6.1 |
| 7 | 1.6 | 2.9 | 4.3 | 4.1 | 3.4 | 3.7 | 4.7 | 5.3 | 6.4 | 6.3 |
| 9 | | | | | | | 4.3 | 3.7 | 6.2 | 6.0 |
| 10 | 1.5 | 2.7 | 3.8 | 4.7 | 3.6 | 3.6 | | 4.8 | | |
| 12 | 1.5 | 3.1 | 3.6 | 4.4 | 3.1 | 3.8 | 4.3 | 5.7 | 5.7 | 5.8 |
| 15 | | | | 3.5 | 3.2 | 3.4 | 4.3 | 5.0 | 4.8 | |

*Results expressed as mEq/L of Ca ion

EXAMPLE 12

Following the procedure of Example 4, ten additional grams of resin having an ion loading of 60 mEq % K, 30 mEq % Ca and 10 mEq % Ma, is prepared, a-d thereafter equilibrated with 25 ml portions of the normal electrolyte solution of Example 1. Each 25 ml eluant is collected, and selected eluants are analyzed. The ion values of the normal electrolyte solution, as determined by analysis, are set forth in Table 6 (see the designation "Normal"). The results are shown in Table 6, as mEq/L of ion.

The results of Examples 1-12 surprisingly demonstrate that it is necessary to load an alkali metal ion-charged, cation exchange resin with at least about 15 mEq % Ca and about 5 mEq % Mg.

TABLE 6

| Portion | Na | K | Ca | Mg |
|---|---|---|---|---|
| Normal | 135.0 | 4.2 | 5.1 | 1.6 |
| 2 | 21.0 | 112.0 | 6.6 | 2.1 |
| 7 | 92.0 | 53.0 | 5.2 | 1.5 |

EXAMPLE 13

10 g of the resin starting material of Example 1, is converted to a treated resin having an ion loading of 56.8 mEq % Na, 31.6 mEq % Ca and 11.6 mEq % Mg; and thereafter equilibrated with 25 ml portions of the normal electrolyte solution of Example 1. Each 25 ml eluant is collected, and selected eluants are analyzed. The ion values of the normal electrolyte solution, as determined by analysis, are set forth in Table 7 (see the designation "Normal"). The results are shown in Table 7, as mEq/L of

TABLE 7

| Portion | Na | K | Ca |
|---|---|---|---|
| Normal | 140.0 | 4.0 | 4.8 |
| 1 | 126.0 | 0.2 | 4.8 |
| 3 | 149.7 | 0.2 | 5.7 |
| 5 | 150.5 | 0.5 | 5.8 |
| 7 | 149.6 | 1.0 | 6.3 |
| 9 | 151.8 | 1.4 | 6.0 |
| 12 | 140.5 | 2.8 | 6.1 |

The above examples are illustrative of the present invention. It is to be understood that these examples are not in any way to be interpreted as limiting the scope of the invention. Rather, it is intended that the scope of the invention be defined by the claims set forth below. I contemplate that the invention as hereinafter claimed, will be subject to various modifications, which modifications are within the scope thereof.

APPLICABILITY

The alkali metal cation-loaded, cation exchange resin of this invention is useful for the treatment of the hypernatremic or hyperkalemic patient. Additionally, in one embodiment, the resin is useful for patients also having low blood calcium levels.

I claim:

1. A pharmaceutical composition comprising a water-insoluble, non-bioabsorbable, cation-charged, cation exchange resin charged with cations consisting essentially of about 80–40 mEq % of an alkali metal ion selected from the group consisting of sodium and potassium, about 15–50 mEq % of calcium ion, and about 5–13 mEq % of magnesium ion, and a pharmaceutically acceptable carrier; said resin being a polystyrene sulfonate.

2. The pharmaceutical composition of claim 1, wherein said cation exchange resin is charged with about 20–38 mEq % of said calcium ion, and about 7–13 mEq % of said magnesium ion.

3. The pharmaceutical composition of claim 2, wherein said cation exchange resin is charged with about 29–33 mEq % of said calcium ion, and about 9–12 mEq % of said magnesium ion.

4. The pharmaceutical composition of claim 1, wherein said cation exchange resin is charged with about 35-50 mEq % of said calcium ion.

5. The pharmaceutical composition of claim 1, wherein said cation exchange resin is potassium polystyrene sulfonate, said alkali metal cation being potassium.

6. The pharmaceutical composition of claim 1, wherein said cation exchange resin is sodium polystyrene sulfonate, said alkali metal cation being sodium.

7. A treatment for decreasing sodium body fluid levels and increasing potassium body fluid levels, which comprises administering to a host in need of such treatment, a therapeutically effective amount of the pharmaceutical composition of claim 1, wherein said alkali metal cation is potassium.

8. A treatment for decreasing sodium body fluid levels and increasing potassium body fluid levels, and for also increasing calcium body fluid levels, which comprises administering to a host in need of such treatment, a therapeutically effective amount of the pharmaceutical composition of claim 4, wherein said alkali metal cation is potassium.

9. A treatment for decreasing potassium body fluid levels, which comprises administering to a host in need of such treatment, a therapeutically effective amount of the pharmaceutical composition of claim 1, wherein said alkali metal cation is sodium.

10. A treatment for decreasing potassium body fluid levels and for increasing calcium body fluid levels, which comprises administering to a host in need of such treatment, a therapeutically effective amount of the pharmaceutical composition of claim 4, wherein said alkali metal cation is sodium.

11. A pharmaceutical composition comprising a water-insoluble, non-bioabsorbable, cation exchange resin loaded substantially full of physiologically active cations, said cations consisting essentially of about 80-40 mEq % of an alkali metal ion selected from the group consisting of sodium and potassium, about 15-50 mEq % of calcium ion, and about 5-13 mEq % of magnesium ion, and a pharmaceutically acceptable carrier; said resin being a polystyrene sulfonate.

12. The pharmaceutical composition of claim 11, wherein said cation exchange resin is charged with about 20-38 mEq % of said calcium ion, and about 7-13 mEq % of said magnesium ion.

13. The pharmaceutical composition of claim 12, wherein said cation exchange is charged with about 29-33 mEq % of said calcium ion, and about 9-12 mEq % of said magnesium ion.

14. The pharmaceutical composition of claim 11, wherein said cation exchange resin is charged with about 35-50 mEq % of said calcium ion.

15. The pharmaceutical composition of claim 11, wherein said cation exchange resin is potassium polystyrene sulfonate, said alkali metal cation being potassium.

16. The pharmaceutical composition of claim 11, wherein said cation exchange resin is sodium polystyrene sulfonate, said alkali metal cation being sodium.

17. A treatment for decreasing sodium body fluid levels and increasing potassium body fluid levels, which comprises administering to a host in need of such treatment, a therapeutically effective amount of a pharmaceutical composition comprising a water-insoluble, non-bioabsorbable, cation exchange resin loaded substantially full of physiologically active cations, said cations consisting essentially of about 80-40 mEq % of potassium ion, about 15-50 mEq % of calcium ion, and about 5-13 mEq % of magnesium ion, and a pharmaceutically acceptable carrier.

18. A treatment for decreasing sodium body fluid levels and increasing potassium body fluid levels, and for also increasing calcium body fluid levels, which comprises administering to a host in need of such treatment, a therapeutically effective amount of a pharmaceutical composition comprising a water-insoluble, non-bioabsorbable, cation exchange resin loaded substantially full of physiologically active cations, said cations consisting essentially of about 80-40 mEq % of potassium ion, about 15-50 mEq % of calcium ion, and about 5-13 % of magnesium ion, and a pharmaceutically acceptable carrier; wherein said cation exchange resin is charged with about 35-50 mEq % of said calcium ion.

19. A treatment for decreasing potassium body fluid levels, which comprises administering to a host in need of such treatment, a therapeutically effective amount of a pharmaceutical composition comprising a water-insoluble, non-bioabsorbable, cation exchange resin loaded substantially full of physiologically active cations, said cations consisting essentially of about 80-40 mEq % of sodium ion, about 15-50 mEq % calcium ion, and about 5-13 mEq % of magnesium ion, and a pharmaceutically acceptable carrier.

20. A treatment for decreasing potassium body fluid levels and for increasing calcium body fluid levels, which comprises administering to a host in need of such treatment, a therapeutically effective amount of a pharmaceutical composition comprising a water-insoluble, non-bioabsorbable, cation exchange resin loaded substantially full of physiologically active cations, said cations consisting essentially of about 80-40 mEq % of sodium ion, about 15-50 mEq % of calcium ion, and about 5-13 mEq % of magnesium ion, and a pharmaceutically acceptable carrier, wherein said cation exchange resin is charged with about 35-50 mEq % of said calcium ion.

* * * * *